United States Patent
Kim et al.

(10) Patent No.: US 10,588,602 B2
(45) Date of Patent: Mar. 17, 2020

(54) PORTABLE ULTRASOUND APPARATUS AND CONTROL METHOD FOR THE SAME

(71) Applicant: SAMSUNG ELECTRONICS CO., LTD., Suwon-si (KR)

(72) Inventors: Bae Hyung Kim, Yongin-si (KR); Kyu Hong Kim, Seoul (KR); Su Hyun Park, Hwaseong-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 960 days.

(21) Appl. No.: 15/040,324

(22) Filed: Feb. 10, 2016

(65) Prior Publication Data
US 2016/0228092 A1 Aug. 11, 2016

(30) Foreign Application Priority Data
Feb. 10, 2015 (KR) .................. 10-2015-0020275

(51) Int. Cl.
*A61B 8/14* (2006.01)
*A61B 8/00* (2006.01)
(Continued)

(52) U.S. Cl.
CPC .......... *A61B 8/4427* (2013.01); *A61B 8/5207* (2013.01); *G01S 7/5208* (2013.01); *G01S 7/52025* (2013.01); *G01S 7/52082* (2013.01); *G01S 7/52084* (2013.01); *G01S 15/8915* (2013.01); *A61B 8/14* (2013.01); *A61B 8/54* (2013.01)

(58) Field of Classification Search
CPC ....... A61B 8/4427; A61B 8/5207; A61B 8/54; A61B 8/14; G01S 7/5208; G01S 7/52082; G01S 15/8915; G01S 7/52025; G01S 7/52084
See application file for complete search history.

(56) References Cited

U.S. PATENT DOCUMENTS 5,477,858 A 12/1995 Norris et al.
5,531,224 A * 7/1996 Ellis .................... G01S 7/52044
600/437

(Continued)

FOREIGN PATENT DOCUMENTS

KR 20110037706 A * 4/2011
KR 10-2012-0090470 A 8/2012

OTHER PUBLICATIONS

Pridham et al., "Digital Interpolation Beamforming for low-Pass and Bandpass Signals," Jun. 1979, Proceedings of the IEEE, vol. 67, No. 6, pp. 904-919 (Year: 1979).*

(Continued)

*Primary Examiner* — Mark D Remaly
(74) *Attorney, Agent, or Firm* — Sughrue Mion, PLLC

(57) ABSTRACT

A portable ultrasound apparatus includes a sampler configured to obtain an in-phase signal and a quadrature signal from an ultrasound signal; a memory configured to store the in-phase signal and the quadrature signal and output the stored in-phase signal and the stored quadrature signal according to a first time delay; an interpolator configured to interpolate the in-phase signal and the quadrature signal outputted from the memory; and a phase rotator configured to apply a second time delay to the interpolated in-phase signal and the interpolated quadrature signal.

19 Claims, 14 Drawing Sheets

(51) Int. Cl.
*A61B 8/08* (2006.01)
*G01S 15/89* (2006.01)
*G01S 7/52* (2006.01)

(56) References Cited

U.S. PATENT DOCUMENTS

| | | | | |
|---|---|---|---|---|
| 5,617,862 | A * | 4/1997 | Cole | G01S 15/8913 600/459 |
| 5,904,652 | A | 5/1999 | Gilbert et al. | |
| 6,390,980 | B1 | 5/2002 | Peterson et al. | |
| 7,901,358 | B2 * | 3/2011 | Mehi | G01S 7/52017 600/447 |
| 2004/0015079 | A1 * | 1/2004 | Berger | G01S 7/52028 600/437 |
| 2004/0138564 | A1 | 7/2004 | Hwang et al. | |
| 2005/0124890 | A1 | 6/2005 | Halmann et al. | |
| 2005/0154304 | A1 | 7/2005 | Robinson | |
| 2007/0016022 | A1 * | 1/2007 | Blalock | G01S 7/52028 600/437 |
| 2007/0239001 | A1 * | 10/2007 | Mehi | G01S 7/52017 600/437 |
| 2007/0239019 | A1 * | 10/2007 | Richard | A61B 8/00 600/459 |
| 2008/0009726 | A1 * | 1/2008 | Bae | A61B 8/06 600/455 |
| 2008/0110261 | A1 * | 5/2008 | Randall | A61B 8/06 600/455 |
| 2009/0088641 | A1 * | 4/2009 | Baba | A61B 8/06 600/455 |
| 2011/0054296 | A1 * | 3/2011 | McCarthy | A61B 5/742 600/407 |
| 2013/0109969 | A1 * | 5/2013 | Kim | H04B 1/06 600/443 |
| 2013/0158366 | A1 | 6/2013 | Bogineni et al. | |
| 2013/0178744 | A1 * | 7/2013 | Kierulf | A61B 8/4427 600/459 |
| 2013/0184587 | A1 * | 7/2013 | Eom | A61B 8/4411 600/443 |
| 2013/0281863 | A1 * | 10/2013 | Chiang | A61B 5/0066 600/425 |
| 2014/0187925 | A1 * | 7/2014 | Corl | A61B 5/0066 600/425 |
| 2014/0351206 | A1 * | 11/2014 | Lim | G06F 9/44526 707/609 |
| 2015/0038844 | A1 * | 2/2015 | Blalock | A61B 8/4427 600/440 |
| 2015/0374346 | A1 * | 12/2015 | Manigoff | A61B 8/56 600/437 |

OTHER PUBLICATIONS

Fenster et al., "Three dimensional ultrasound imaging," 2001, Physics in Medicine and Biology, vol. 46, pp. R67-R99 (Year: 2001).*

Aamir et al., "On Cooley-Tukey FFT Method for Zero Padded Signals," Sep. 17-18 2005, In Proceedings of IEEE International Conference on Emerging Technologies, Islamabad (Year: 2005).*

Yoon et al., "Display pixel based focusing using multi-order sampling for medical ultrasound imaging," Dec. 2009, Electronics Letters, vol. 45, No. 25, pp. 1292-1293 (Year: 2009).*

Kim, KR-20110037706-A, Apr. 2011, Machine Translated English (Year: 2011).*

* cited by examiner

| I (0) | Q (1) | -I (2) | -Q (3) | I (4) | Q (5) | . . . ...... |

FIG.5

PORTABLE ULTRASOUND APPARATUS AND CONTROL METHOD FOR THE SAME

CROSS-REFERENCE TO RELATED APPLICATION(S)

This application claims the benefit of Korean Patent Application No. 2015-0020275, filed on Feb. 10, 2015 in the Korean Intellectual Property Office, the disclosure of which is incorporated herein by reference in its entirety.

BACKGROUND

1. Field

Exemplary embodiments relate to a portable ultrasound apparatus configured to perform a beamforming echo signal operation and a control method thereof.

2. Description of Related Art

An ultrasound apparatus irradiates ultrasonic waves to a target part in an object through the surface of the object, detects echo ultrasonic waves reflected from the object and then noninvasively acquires images used to generate a tomogram of a soft tissue or bloodstream.

An ultrasound apparatus is compact, inexpensive, and displays a diagnostic imaging in real time as compared with other types of diagnostic imaging apparatuses, e.g., an X-ray device, a Computerized Tomography (CT) scanner, a Magnetic Resonance Image (MRI), or a diagnostic nuclear medical apparatus. In addition, the ultrasound apparatus is safe because there is no risk of radiation exposure. Therefore, the ultrasound apparatus is widely used in medical examinations in various fields, such as cardiology, abdomen examination, and urology clinics and maternity clinics, and is particularly used for the diagnosis of a fetus.

SUMMARY

Therefore, it is an aspect of the exemplary embodiments to provide a portable ultrasound apparatus configured to perform efficient beamforming, and a control method thereof.

Additional aspects of the present disclosure will be set forth in part in the description which follows and, in part, will be apparent from the description, or may be learned by practice of the exemplary embodiments.

In accordance with an aspect of an exemplary embodiment, a portable ultrasound apparatus includes a sampler configured to obtain an in-phase signal and a quadrature signal from an ultrasound signal, a memory configured to store the in-phase signal and the quadrature signal and output the stored in-phase signal and the stored quadrature signal according to a first time delay, an interpolator configured to interpolate the in-phase signal and the quadrature signal outputted from the memory, and a phase rotator configured to apply a second time delay to the interpolated in-phase signal and the interpolated quadrature signal.

In accordance with an aspect of another exemplary embodiment, a control method to be performed by a portable ultrasound apparatus includes obtaining an in-phase signal and a quadrature signal from an ultrasound signal and storing the obtained in-phase signal and the obtained quadrature signal, performing a first delay operation to output the stored in-phase signal and the stored quadrature signal according to a first time delay, interpolating the output in-phase signal and the output quadrature signal, and performing a second delay operation to apply a second time delay to the interpolated in-phase signal and the interpolated quadrature signal.

BRIEF DESCRIPTION OF THE DRAWINGS

These and/or other aspects of the exemplary embodiments will become apparent and more readily appreciated from the following description of the exemplary embodiments, taken in conjunction with the accompanying drawings of which:

FIG. 5 is a view illustrating storing of an in-phase signal and a quadrature signal in an interleaved manner;

DETAILED DESCRIPTION

An ultrasound diagnosis system and a control method thereof will be described with reference to the accompanying drawings.

Figure 1:
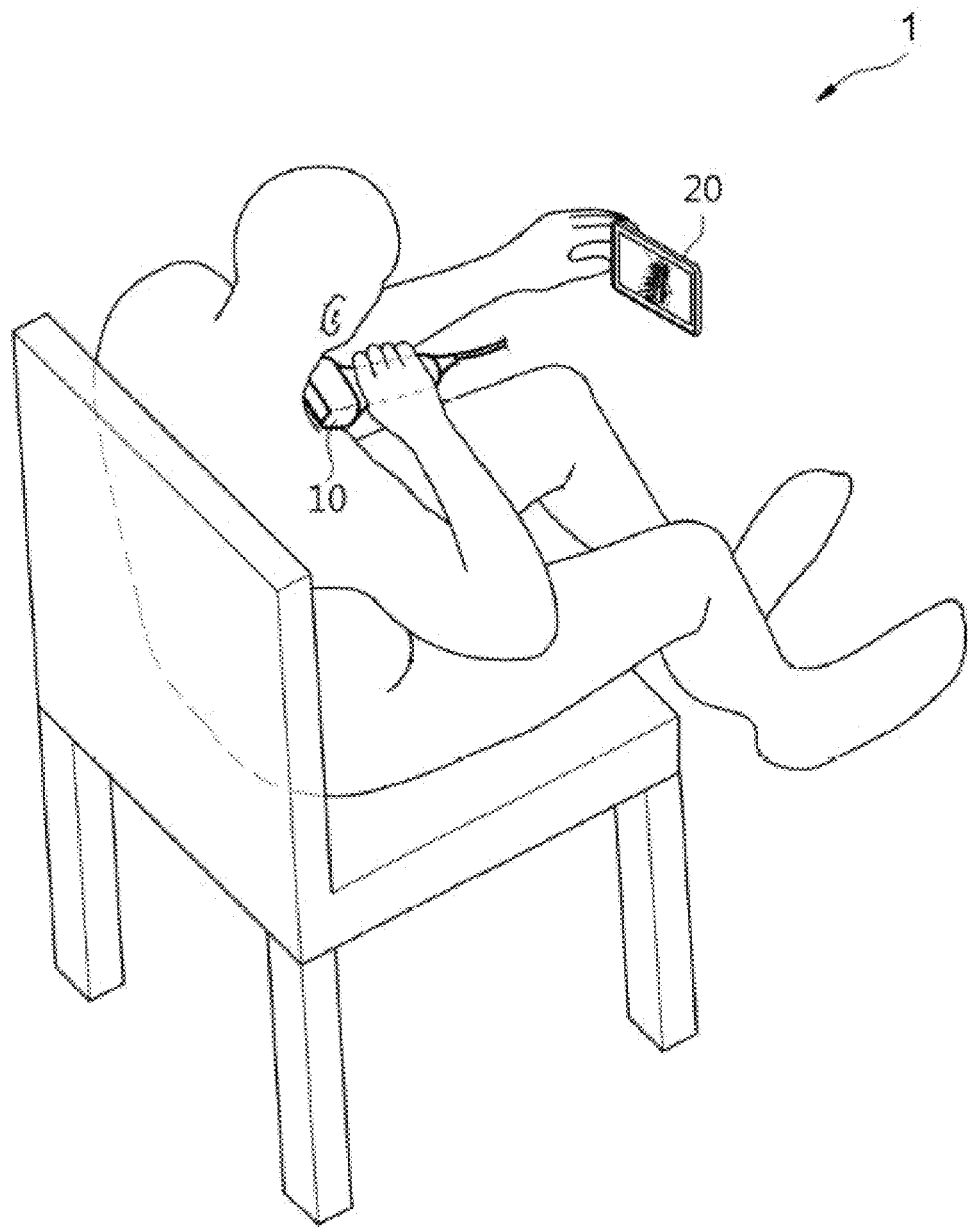
FIG. 1 is a view illustrating an example of using an ultrasound diagnosis system in accordance with an exemplary embodiment.
Figure 2:
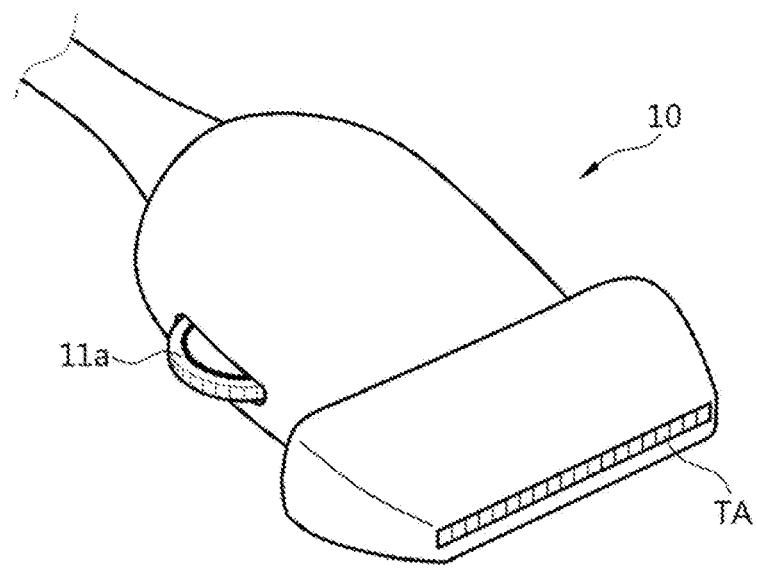
FIG. 2 is a view illustrating an example of a portable ultrasound apparatus provided with a one-dimensional transducer array in accordance with an exemplary embodiment.
Figure 3:
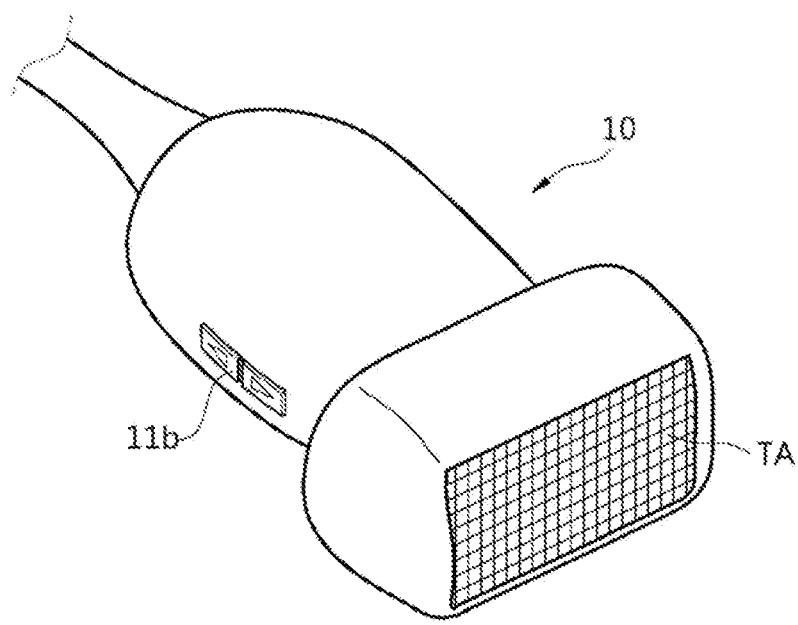
FIG. 3 is a view illustrating a portable ultrasound apparatus provided with a two-dimensional transducer array in accordance with an exemplary embodiment.

FIG. 1 is a view illustrating an example of using an ultrasound diagnosis system in accordance with an exemplary embodiment, FIG. 2 is a view illustrating a portable ultrasound apparatus provided with a one-dimensional array transducer in accordance with an exemplary embodiment, and FIG. 3 is a view illustrating a portable ultrasound apparatus provided with a two-dimensional array transducer in accordance with an exemplary embodiment.

Referring to FIG. 1, an ultrasound diagnosis system 1 in accordance with an exemplary embodiment may include a portable ultrasound apparatus 10 to generate a composite signal by beamforming an ultrasound signal reflected from an object and a user terminal 20 to generate an ultrasound image based on the combined signal received from the portable ultrasound apparatus 10 and to display the ultrasound image. An object may be a living body, such as a human or animal, but is not limited thereto. Anything having a structure that is capable of being imaged by an ultrasound signal may be considered an object.

As illustrated in FIG. 1, a user may hold the portable ultrasound apparatus 10 with one hand, and may hold the user terminal 20 with the other hand so that an ultrasound image may be easily provided.

As illustrated in FIGS. 2 and 3, the portable ultrasound apparatus 10 may be formed in a shape which enables the user to hold the portable ultrasound apparatus 10 easily. In a front end of the portable ultrasound apparatus 10, a transducer array (TA) may be provided to transmit an ultrasound signal to an object by making contact with a surface of the object, and to receive an ultrasound signal reflected from the object.

The TA converts an electrical signal into an ultrasound signal, and transmits the ultrasound signal to an object. The ultrasound signal transmitted to the object is reflected inside the object and then inputted into the TA. The TA outputs an echo signal in the form of alternating current (AC) by vibrating in a frequency corresponding to a frequency of the ultrasound signal reflected from the inside of the object.

The TA may include a plurality of transducer elements. The transducer elements may convert an ultrasound signal into an electrical signal and vice versa. For this feature, the TA may be implemented as magnetostrictive ultrasonic transducers using the magnetostrictive effect of a magnetic material, piezoelectric ultrasonic transducers using the piezoelectric effect of a piezoelectric material, piezoelectric micromachined ultrasonic transducers (pMUT), or capacitive micromachined ultrasonic transducers (cMUT) that transmit and receive ultrasonic waves using vibration of several hundreds or thousands of micromachined thin films.

As illustrated in FIG. 2, the TA may be formed in a one-dimensional array, or as illustrated in FIG. 3, may be formed in a two-dimensional array. In addition, the TA arranged in a linear manner is illustrated in FIG. 2, but the TA may be arranged in a convex manner or another manner altogether.

The user terminal 20 may be connected to the portable ultrasound apparatus 10 by using a wired or wireless communication, and may receive data from the portable ultrasound apparatus 10. The user terminal 20 may generate an ultrasound image based on data received from the portable ultrasound apparatus 10, and may display the ultrasound image to a user.

The user terminal 20 may include a general purpose apparatus, such as a Portable Media Player (PMP), Personal Digital Assistant (PDA), Tablet PC, and smart phone. That is, the user terminal 20 may generate and display an ultrasound image by using general purpose hardware. Hereinafter, a detailed description of components constituting the ultrasound diagnosis system 1 will be described.

Figure 4:
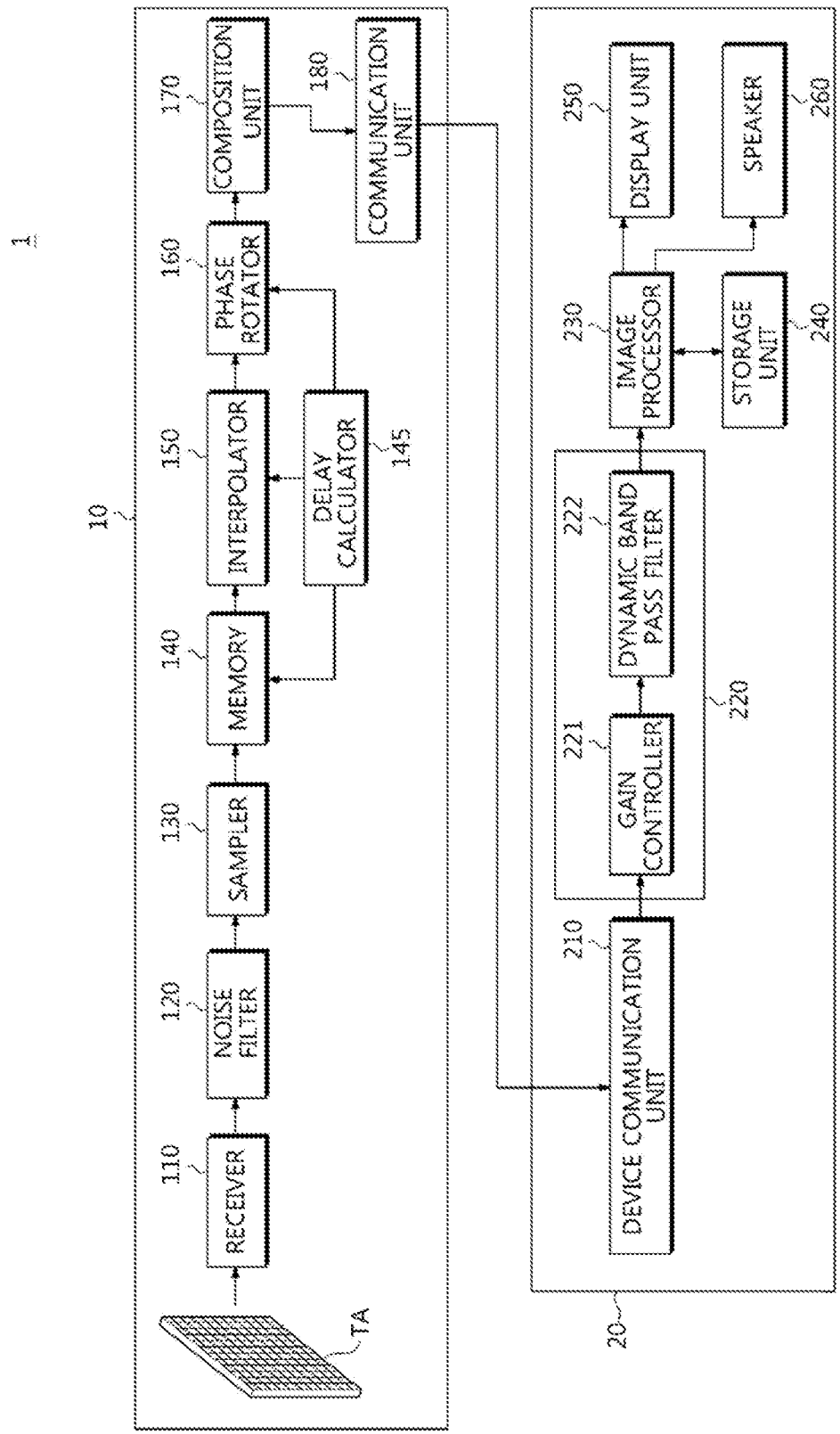
FIG. 4 is a control block diagram illustrating an ultrasound diagnosis system in accordance with an exemplary embodiment.

FIG. 4 is a control block diagram illustrating an ultrasound diagnosis system in accordance with an exemplary embodiment.

Referring to FIG. 4, the portable ultrasound apparatus 10 may include a receiver 110, a noise filter 120, a sampler 130, a memory 140, an interpolator 150, a phase rotator 160, a composition unit 170, and a communication unit 180. The receiver 110, the noise filter 120, the sampler 130, the memory 140, and the interpolator 150 may be provided in the transducer element.

The receiver 110 may be connected to the transducer element and receive an echo signal outputted from the transducer element. In addition, the receiver 110 may amplify the received echo signal and output the amplified echo signal.

To amplify an echo signal, the receiver 110 may include at least one of a Low Noise Amplifier (LNA) to reduce a noise in the echo signal, a Variable Gain Amplifier (VGA) to control a gain value according to a focal point, and a preamp. The VGA may be a Time Gain Compensation amplifier (TGC) to compensate a gain according to a distance to a focal point, but is not limited thereto.

The noise filter 120 may remove a noise from the echo signal outputted from the receiver 110. The noise filter 120 may remove the noise of the echo signal by performing a low-band pass filtering on an input echo signal. For example, the noise filter 120 may be an anti-aliasing filter to prevent aliasing caused by a high frequency component, but is not limited thereto.

The sampler 130 may perform sampling of an in-phase signal and a quadrature signal from an echo signal in an analog type. The term "sampling" may refer to extracting an in-phase signal and a quadrature signal in a digital type from an echo signal in an analog type.

In-phase signal and quadrature may be used to determine a brightness value (size information of ultrasound signal), and information of a motion (phase information of ultrasound signal) in an ultrasound image.

In addition, the sampler 130 may perform sampling of an in-phase signal and a quadrature signal by using a sampling frequency. The sampling frequency may represent the number of samples per unit time, and may also be referred to as "sampling rate".

As a sampling frequency becomes higher, the number of samples per unit time is increased, and thus a sampling cycle to extract (e.g., obtain) an in-phase signal and a quadrature signal may be shorter. Conversely, as a sampling frequency becomes lower, the number of samples per unit time is reduced, and thus a sampling cycle to extract an in-phase signal and a quadrature signal may be longer. That is, the sampling frequency is inversely proportional to the sampling cycle.

The sampling frequency may be set as a frequency which enables an in-phase signal and a quadrature signal to be directly extracted (e.g., obtained) from an echo signal without a demodulation process. The sampling frequency which enables an in-phase signal and a quadrature signal to be directly extracted from an echo signal without a demodulation process may be determined by sampling theory.

For example, the sampling frequency may be determined by any one of a frequency corresponding to an integer multiple of a center frequency transmitted to an object from the TA and a frequency corresponding to an integer multiple of an echo signal frequency received to the TA.

In a case of directly extracting an in-phase signal and a quadrature signal from an echo signal by using a sampling frequency, the in-phase signal and the quadrature signal may be sampled to be mutually interleaved.

Hereinafter, a sampling method using a sampling frequency corresponding to four times of a center frequency will be described with reference to FIGS. 1 to 4. An echo signal may be expressed as the sum of an in-phase signal and a quadrature signal according to the following equation 1.

$$r(nT_s) = r_I(nT_s)\cos(2\pi f_r nT_s) + r_Q(nT_s)\sin(2\pi f_r nT_s) \quad \text{Equation 1}$$

In equation 1, r represents an echo signal, $r_I$ represents an in-phase signal, $r_Q$ represents a quadrature signal, n represents the number of sampling, $T_s$ represents a sampling cycle, and fr represents a center frequency.

When a sampling frequency is set as four times of a center frequency, a sampling cycle and a sampling frequency may be represented according to the following equation 2.

$$T_s = \frac{1}{4f_r} \quad \text{Equation 2}$$

When equation 1 is substituted into equation 2, an in-phase signal and a quadrature signal may be described according to the following equation 3.

$$r(nT_s) = r_I(nT_s)\cos\left(\frac{n\pi}{2}\right) + r_Q(nT_s)\sin\left(\frac{n\pi}{2}\right) \quad \text{Equation 3}$$

The number of samples (n) may be an integer, and thus, a Cos component and a Sin component in equation 3 may be changed into per $\pi/2$. Therefore, a Cos component and a Sin component may be an integer, such as −1, 0, and 1.

As mentioned above, by using the sampling frequency, a Cos component in an in-phase signal and a Sin component in a quadrature signal may have only an integer value, and thus the sampler 130 may extract an in-phase signal and a quadrature signal from an echo signal without an additional demodulation process. That is, the sampler 130 may be implemented without a hardware device for the demodulation, such as cos look-up table, sin look-up table, and multiplication, and thus the complexity of the portable ultrasound apparatus 10 may be reduced and the portable ultrasound apparatus 10 may be miniaturized.

Particularly, an in-phase signal and a quadrature signal, which are sequentially extracted according to a sampling frequency, which is four times of the center frequency, may be described according to the following equation 4.

$$r(0) = r_I(0) = I(0) \quad \text{Equation 4}$$
$$r(T_s) = r_Q(T_s) = Q(1)$$
$$r(2T_s) = -r_I(2T_s) = -I(2)$$
$$r(3T_s) = -r_Q(3T_s) = -Q(3)$$
$$r(4T_s) = r_I(4T_s) = I(4)$$
$$r(5T_s) = r_Q(5T_s) = Q(5)$$
$$r(6T_s) = -r_I(6T_s) = -I(6)$$
$$r(7T_s) = -r_Q(7T_s) = -Q(7)$$
$$\vdots$$

As mentioned above, when performing the sampling by using a sampling frequency, an in-phase signal and a quadrature signal may be extracted in an interleaved manner.

The memory 140 may store the in-phase signal and the quadrature signal sampled by the sampler 130. The in-phase signal and the quadrature signal may be stored in an interleaved manner.

Figure 5:
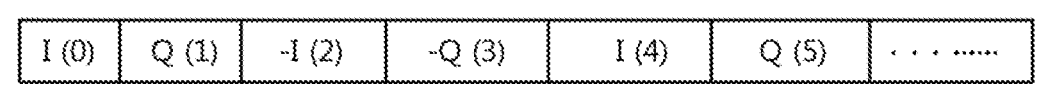

FIG. 5 is a view illustrating storing of an in-phase signal and a quadrature signal in an interleaved manner. Referring to FIG. 5, an in-phase signal and a quadrature signal sampled by the sampler 130 may be stored in an interleaved manner in the memory 140.

When sampling an in-phase signal and a quadrature signal by using a sampling frequency, as illustrated in equation 4, the in-phase signal and the quadrature signal may be alternately extracted. The memory 140 may store the in-phase signal and the quadrature signal, which are alternately sampled in the sampler 130, to be disposed in an interleaved manner, as illustrated in FIG. 5.

As mentioned above, by storing the in-phase signal and the quadrature signal in an interleaved manner, the capacity of the memory 140 to store the in-phase signal and the quadrature signal may be reduced and the load caused by the input or output of the memory 140 may be reduced.

The delay calculator 145 may calculate a delay period of time to be applied to a sampling signal. At this time, the sampling signal may represent at least one signal of the in-phase signal and the quadrature signal, which are sampled by the sampler 130.

A distance between a focal point and each transducer element may be different from each other. Due to the difference in the distance between the focal point and each transducer element, an echo signal reflected from the focal point may be outputted from a transducer element with a certain time difference. Particularly, a transducer element close to the focal point may firstly output an echo signal, and a transducer element far from the focal point may output an echo signal later.

The delay calculator 145 may calculate a delay period of time of a sampling signal to compensate a time difference of an echo signal caused by the differences in the distance between the transducer element and the focal point. Particularly, the delay calculator 145 may calculate a coarse delay and a fine delay.

The coarse delay may represent an approximate delay period of time, which is adjustable by adjusting an output timing of a sample signal stored in the memory 140, and the output timing of the sample signal stored in the memory 140 may be adjusted according to a coarse delay value.

The fine delay may be to compensate a delay period time, which is shorter than a sampling cycle, and may be applied by the interpolator and the phase rotator, which will be described later. Hereinafter, the coarse delay and the fine delay will be described in detail with reference to FIGS. 6A and 6B.

Figure 6A:
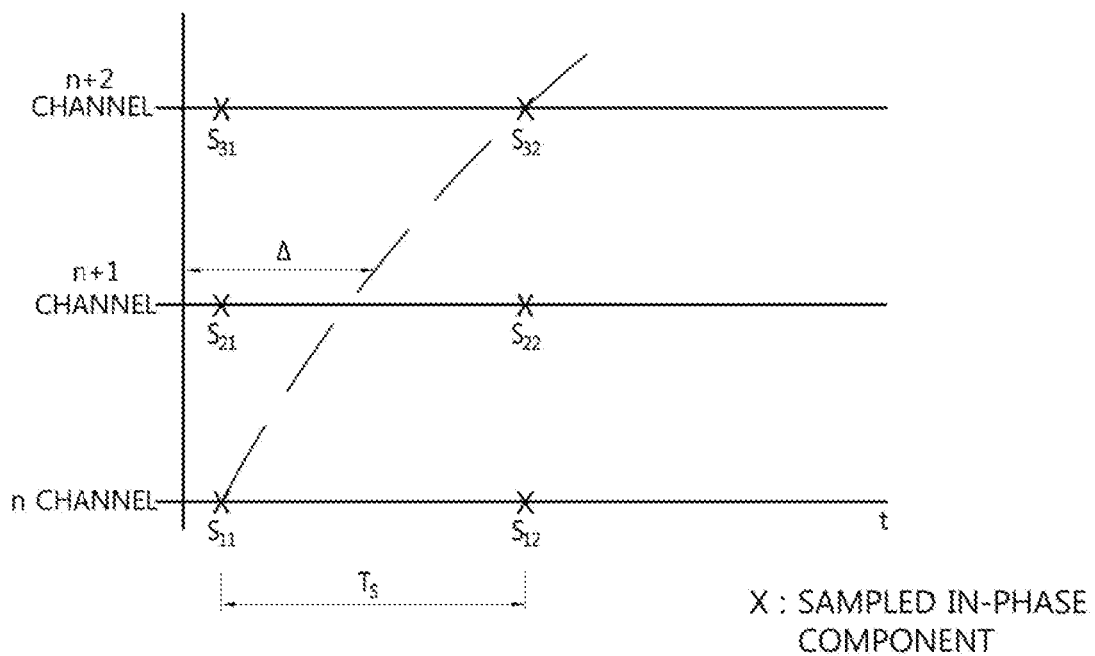
FIG. 6A is a view illustrating a coarse delay.
Figure 6B:
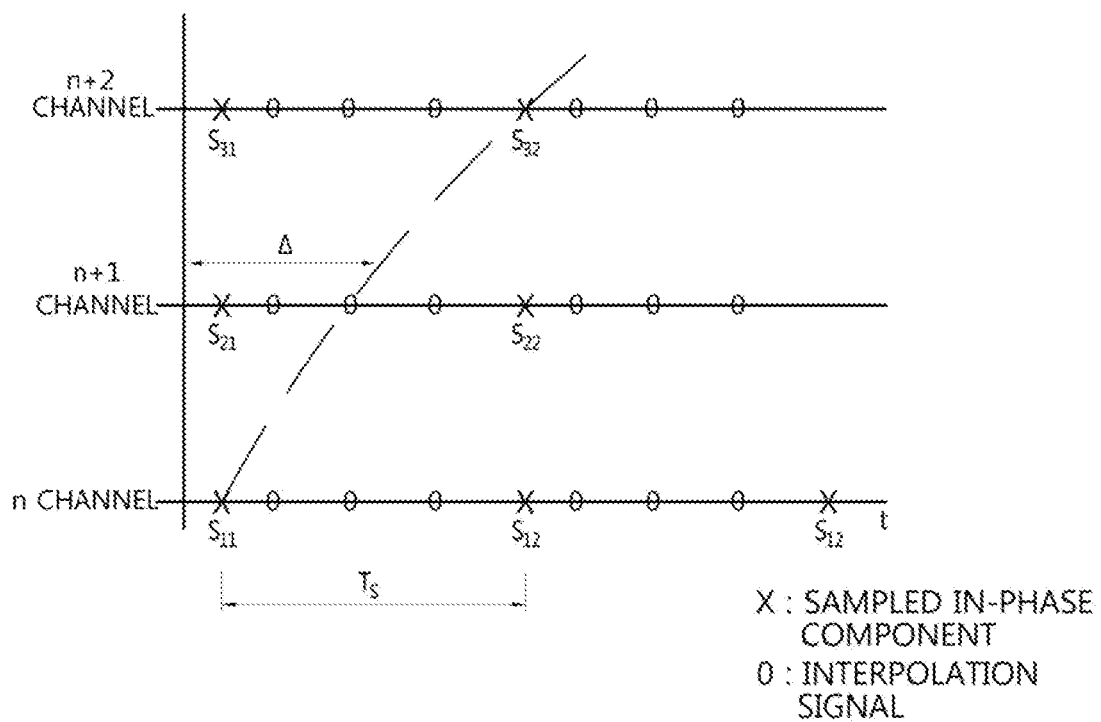
FIG. 6B is a view illustrating a fine delay.

FIG. 6A is a view illustrating a coarse delay and FIG. 6B is a view illustrating a fine delay. A vertical direction of FIG. 6 may represent a channel of a transducer element, and a horizontal direction of FIG. 6 may represent a flow of time.

Referring to FIG. 6A, a sampling signal ($S_{11}$ to $S_{32}$) sampled by a sampling cycle $T_s$ may be stored sequentially in the memory 140.

When a time difference, which is caused by a distance difference between a transducer element and a focal point, is represented by a dotted line of FIG. 6, a time difference may be $T_s$ between a sampling signal $S_{11}$ in n channel and a sampling signal $S_{32}$ in n+2 channel.

Therefore, the delay calculator 145 may calculate a coarse delay so that a first sampling signal $S_{11}$ in n channel and a second sampling signal $S_{32}$ in n+2 channel may be outputted together from the memory.

However, a time difference ($\Delta$) in a channel having a time difference shorter than a sampling cycle $T_s$, such as a n+1 channel, may not be compensated by the coarse delay. By increasing a sampling frequency so that the sampling cycle TS is to correspond to the time difference ($\Delta$), the time difference may be compensated. However, since increasing a sampling frequency results in the number of samples per unit time to be increased, hardware having a high performance may be required and the capacity of the memory to store the sampling signal may need to be increased.

Accordingly, the portable ultrasound apparatus in accordance with an exemplary embodiment may increase a sampling frequency by interpolating the sampled signal, and may apply a fine delay to the interpolated signal.

The interpolator 150 may increase a sampling frequency of a sampling signal by interpolating the sampling signal.

Particularly, as illustrated in FIG. 6B, the interpolator 150 may perform zero padding to insert an interpolation signal 0 (zero) between sampling signals, and may increase a sampling frequency by passing a sampling signal, into which the interpolation signal is inserted, through an interpolation filter.

In addition, the interpolator 150 may interpolate a sampling signal based on a fine delay value. Particularly, the interpolator 150 may determine a sampling frequency, which is needed to apply the fine delay value, and may increase the sampling frequency of the sampling signal up to a determined sampling frequency.

At this time, the increased sampling frequency may be determined by an interpolation signal inserted between the sampling signals. For example, when a sampling frequency is $f_0$, and three zeros are padded between sampling signals, the sampling frequency may be increased to 4 $f_0$.

A low band pass filter may be used as the interpolation filter, and the error rate of the interpolator 150 may be reduced as the low band pass filter order is increased. However, as the low band pass filter order is increased, the number of multipliers used may be increased, and thus the low band pass filter order may be determined in consideration of the performance of the interpolator 150 and the complexity of the hardware.

Two of the interpolators 150 may be provided in each channel respectively to interpolate each in-phase signal and each quadrature signal. In addition, when the in-phase signal and the quadrature signal are stored in an interleaved manner, the in-phase signal and the quadrature signal may be alternately interpolated by one single interpolator 150.

The phase rotator 160 may apply a fine delay to the interpolated sampling signal. Particularly, the phase rotator 160 may convert a fine delay estimated by the delay calculator 145 into the shape of a delay phase, and may apply a fine time delay to the in-phase signal and the quadrature signal by applying the delay phase to the in-phase signal and the quadrature signal, respectively.

For example, the phase rotator 160 may convert a fine delay (Δ) in n+1 channel into a shape of delay phase, and may apply the fine time delay to the sampling signal by rotating a sampling signal $S_{21}$ in n+1 channel as much as the delay phase.

The composition unit 170 (e.g., compositioner) may generate a composite signal by composing a sampling signal to which a time delay is applied. At this time, the composite signal may include an in-phase composite signal of the in-phase signal, and a quadrature composite signal of the quadrature signal.

When composing the sampling signal, a weighed value may be applied so that a sampling signal outputted from a certain channel may be relatively emphasized or a sampling signal outputted from a certain channel may be relatively attenuated. The weighed value may be divided into data-independent beamforming (fixed beamforming) and data-dependent beamforming (adaptive beamforming) based on an application method. The fixed beamforming method is to apply a predetermined weighed value, which is unrelated to an echo signal, and the adaptive beamforming method is to apply a weight value, which is to be applied to an echo signal, based on an echo signal.

The communication unit 180 (e.g., communicator) may transmit the composite signal generated in the composition unit 170 to the outside of the device. Particularly, the communication unit 180 may output the composite signal to the user terminal 20 by being connected to the user terminal 20. The communication unit 180 may include at least one of a wired communication module, a local communication module and a wireless communication module.

The wire communication module may connect the communication unit 180 to the user terminal 20 by using Peripheral Component Interconnect (PCI), PCI-express, Universe Serial Bus (USB), and the likes.

The local communication module may connect the communication unit 180 to the user terminal 20 by using a local communication method, such as Bluetooth, Bluetooth low energy, Infrared Data Association (IrDA), Zigbee, Wi-Fi, Wi-Fi direct, Ultra Wideband (UWB), and near field communication (NFC).

The wireless communication module may connect the communication unit 180 to the user terminal 20 by using a wireless communication method, such as a communication method based on GSM/3GPP (GSM, HSDPA, LTE advanced), a communication method based on 3GPP2 (CDMA), or a communication method based on Wi-MAX.

The user terminal 20 receiving a composite signal from the portable ultrasound apparatus 10 may generate an ultrasound image based on the composite signal. The user terminal 20 may generate an Amplitude Mode (A-mode) image, a Brightness Mode (B-mode) image, a Motion Mode (M-mode) image, a Color Mode (C-mode) image and a Doppler Mode (D-mode) image, and the user terminal 20 may be optimized to generate a C-mode image, or a D-mode image.

An A-mode image is an ultrasound image indicating the size of a composite signal, a B-mode image indicates the size of a composite signal in the form of a brightness indicated by a plurality of A-mode images in a cross-section, an M-mode image is an ultrasound image indicating a movement in a certain position according to the time, a C-mode image is an ultrasound image indicating a speed of a moving object i.e., blood flow, in a predetermined color mapping, and a D-mode image is an ultrasound image indicating the size and direction of movement of an object in the form of a spectrum.

Particularly, the user terminal 20 may include a device communication unit 210 (e.g., device communicator), a signal processor 220, an image processor 230, a storage unit 240, a display unit 250, and a speaker 260.

The device communication unit 210 may receive data from the external device. Particularly, the device communication unit 210 may be connected to the communication unit 180 of the portable ultrasound apparatus 10 to receive a composite signal from the communication unit 180 of the portable ultrasound apparatus 10. For this feature, the device communication unit 210 may include at least one of the above-mentioned wired communication modules, local communication modules, or wireless communication modules.

The signal processor 220 may pre-process a composite signal. Particularly, the signal processor includes a gain controller 221, and a dynamic band pass filter 222, and the signal processor 220 may pre-process a composite signal so that the composite signal may be appropriately processed to generate an ultrasound image.

When the composite signal is inputted, the gain controller 221 may control a gain of a composite signal and output the composite signal. The dynamic band pass filter 222 may compensate the frequency variation which changes according to the depth of the focal point.

The attenuation of ultrasonic waves irradiated to an object may be determined by characteristics of a medium inside the object and the transmission frequency component. As the attenuation coefficient of the medium becomes larger, and a depth becomes deeper, and a frequency becomes higher, the attenuation may be increased. Therefore, a center frequency of an ultrasound signal irradiated to the object may be different from a center frequency of an echo signal reflected from the object.

A pass band of the dynamic band pass filter 222 may be dynamically adjusted according to the center frequency variation of an echo signal, and thus may compensate the frequency variation according to the depth of the focal point. By compensating the center frequency variation according to the depth of the focal point, a Signal to Noise Ratio (SNR) may be minimized when an ultrasound image is generated.

In addition, the signal processor 220 may be implemented by a general purpose processor provided in the user terminal 20.

The image processor 230 may generate an ultrasound image by using the pre-processed composite signal.

According to an exemplary embodiment, the image processor 230 may generate a D-mode image or a C-mode image. A composite signal may include a Doppler signal reflected from the blood flow having a movement, and a clutter signal reflected from a static tissue except the blood flow. In general, there may be a considerable difference between a signal reflected from the blood flow having a movement and a clutter signal reflected from a static tissue except the blood flow, and several numbers kHz to several tens kHz of the difference may be indicated on the frequency. Accordingly, when separating the two components by using a filter, a high performance filter specification may be required. Therefore, the image processor 230 may perform a signal processing operation to remove a clutter signal, which is as a noise component when a Doppler image is generated.

The clutter signal may be removed by a clutter filter. The clutter filter may be implemented as a high pass filter, but is not limited thereto. For example, the clutter filter may be implemented as an adaptive filter configured to adaptively select an optimized cutoff according to a composite signal.

The image processor 230 may extract a spectrum component by performing Fast Fourier Transform on a composite signal, in which a clutter component is removed, and may generate a D-mode image or a C-mode image based on the extracted spectrum component. For this feature, the image processor 230 may include a Digital Scan Converter (DSC) configured to perform scan conversion.

The image processor 230 may detect the direction of progress of the blood flow. The image processor 230 may perform a Hilbert Transform on a composite signal in which a clutter signal is removed, to extract a forward frequency and a reverse frequency in the blood flow.

Meanwhile, the image processor 230 may be implemented by a general purpose processor provided in the user terminal 20.

The storage unit 240 may store data to drive the user terminal 20. Particularly, the storage unit 240 may store an operating system to drive the user terminal 20, an application to generate and display an ultrasound image, and an ultrasound image.

In addition, the storage unit 240 may include a High-Speed Random Access Memory (RAM), a magnetic disk, static RAM (SRAM), dynamic RAM (DRAM), read-only memory (ROM), and the likes. The storage unit 240 may be provided to be detachable. For example, the storage unit 240 may include a Compact Flash Card, a Secure Digital Card, a Smart Media Card, a Multimedia Card (MMC) or a Memory Stick.

The display unit 250 may display an ultrasound image generated by the image processor 230. For example, the display unit 250 may display any ultrasound image of a C-mode image and a D-mode image.

The display unit 250 may be implemented as a Plasma Display Panel (PDP), an Electronic Paper Display (EPD), a Liquid Crystal Display (LCD), a Light emitting Polymer Display (LPD), an Organic Light-Emitting Diode (OLED), an Active-matrix Organic Light-Emitting Diode (AMOLED) or the like. In addition, the display unit 250 may be implemented as a touch screen, and thus, may receive a control command from a user while displaying an ultrasound image.

The speaker 260 may output a sound corresponding to the blood flow. Particularly, the speaker 260 may provide a certain sound corresponding to a forward and reverse frequency of the blood flow based on the forward frequency and reverse frequency of the blood flow acquired by the image processor 230.

Figure 7:
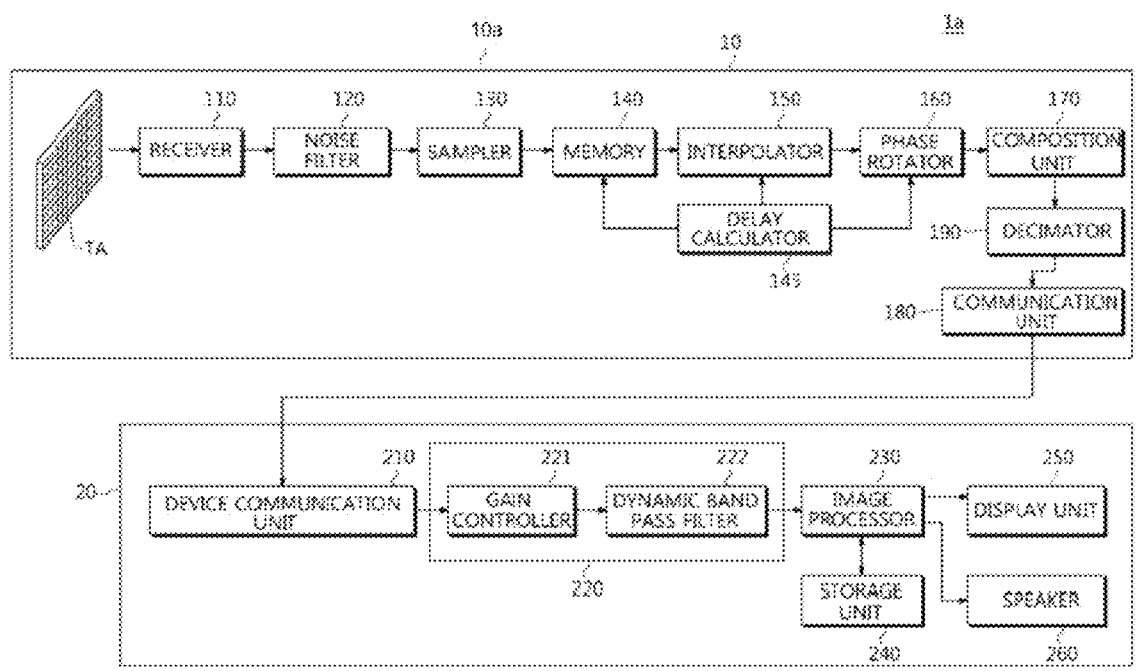
FIG. 7 is a control block diagram illustrating an ultrasound diagnosis system in accordance with another exemplary embodiment.

FIG. 7 is a control block diagram illustrating an ultrasound diagnosis system in accordance with another exemplary embodiment. Among components described in connection with FIG. 7, the same components as those components of the ultrasound diagnosis system 1 according to an exemplary embodiment described in FIG. 4 may have the same reference numerals as the reference numerals of the ultrasound diagnosis system 1 according to an exemplary embodiment, and a detailed description thereof will be omitted.

Referring to FIG. 7, a portable ultrasound apparatus 10a of an ultrasound diagnosis system 1a according to another exemplary embodiment may further include a decimator 190 or a data compressor. As mentioned above, a composite signal acquired by beamforming may be transmitted to the portable ultrasound apparatus 10 and the user terminal 20.

When the composite signal is not smoothly transmitted to the user terminal 20, the generation and display of an ultrasound image may be delayed and thus an ultrasound image may be not provided to a user at real time. The ultrasound diagnosis system 1a according to another exemplary embodiment may relieve the load of the transmission and the reception of the composite signal by using the decimator or data compressor 190.

Particularly, the decimator 190 may be provided between the composition unit 170 and the communication unit 180, and may reduce a sampling frequency of a composite signal outputted by the composition unit 170 and output the composite signal.

The decimator 190 may reduce a sampling frequency of a composite signal by adjusting a sampling cycle of the composite signal to be big. For example, the decimator 190 may adjust the sampling cycle of the composite signal to be 4 times bigger so that a sampling frequency may be reduced from 16 $f_0$ to 4 $f_0$ and outputted.

In addition, the decimator 190 may be implemented by a decimation filter to reduce the sampling frequency, but is not limited thereto.

In FIG. 7, the decimator 190 is illustrated as being disposed between the composition unit 170 and the communication unit 180, but is not limited thereto. For example, the decimator 190 may be disposed between the phase rotator 160 and the composition unit 170 on each channel.

When the decimator 190 is disposed between the phase rotator 160 and the composition unit 170, an in-phase signal and a quadrature signal in which a sampling frequency is reduced may be inputted to the composition unit 170. Therefore, in the composition unit 170, the load of composing a signal may be relieved, and the speed of composing a signal may be improved.

Figure 8:
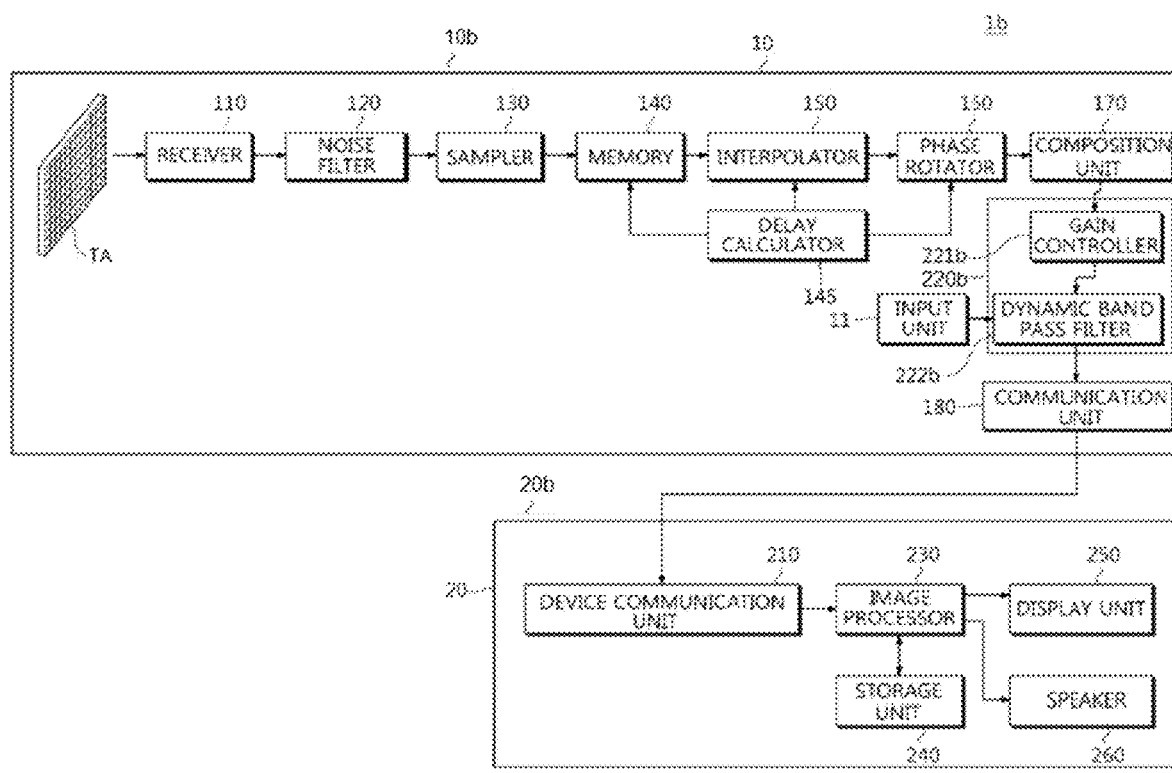
FIG. 8 is a control block diagram illustrating an ultrasound diagnosis system in accordance with another exemplary embodiment.

FIG. 8 is a control block diagram illustrating an ultrasound diagnosis system in accordance with another exemplary embodiment. Among components described in connection with FIG. 8, the same components as the components of the ultrasound diagnosis system 1 according to an exemplary embodiment described in FIG. 4 may have the same reference numerals as the components of the ultrasound diagnosis system 1 according to an exemplary embodiment, and a detailed description thereof will be omitted.

As illustrated in FIG. 8, the ultrasound diagnosis system 1b according to another exemplary embodiment may include a portable ultrasound apparatus 10b and a user terminal 20b. The portable ultrasound apparatus 10b may include a signal processor 220b including a gain controller 221b and a dynamic band pass filter 222b. That is, the portable ultrasound apparatus 10b may perform a pre-process on a composite signal, and the user terminal 20b may generate an ultrasound image based on the pre-processed composite signal.

The portable ultrasound apparatus 10b may perform the pre-process of a composite signal to generate an ultrasound image, and transmit the pre-processed composite signal to the user terminal 20b. Accordingly, the load of processing a signal of the user terminal 20b may be relieved.

In addition, the portable ultrasound apparatus 20b may further include an input unit 11 (e.g., inputter). The input unit 11 may be provided on a side of the portable ultrasound apparatus 10b, and may receive an input of a setting a depth of a focal point from a user.

The input unit 11 may be implemented as various input devices. For example, the input unit 11 may be implemented as a wheel input device 11a as illustrated in FIG. 2, or may be implemented as a touch input device 11b as illustrated in FIG. 3.

As mentioned above, a pre-processing of a signal processor 220b may be different according to the depth of the focal point, and thus the signal processor 220b may perform the pre-processing to correspond to a depth of a focal point, which is set via the input unit 11.

Particularly, a pass band of a dynamic band pass filter 222b may be dynamically changed according to the depth of the focal point, which is set via the input unit 11, and thus may compensate the frequency variation according to the depth of the focal point.

Figure 9:
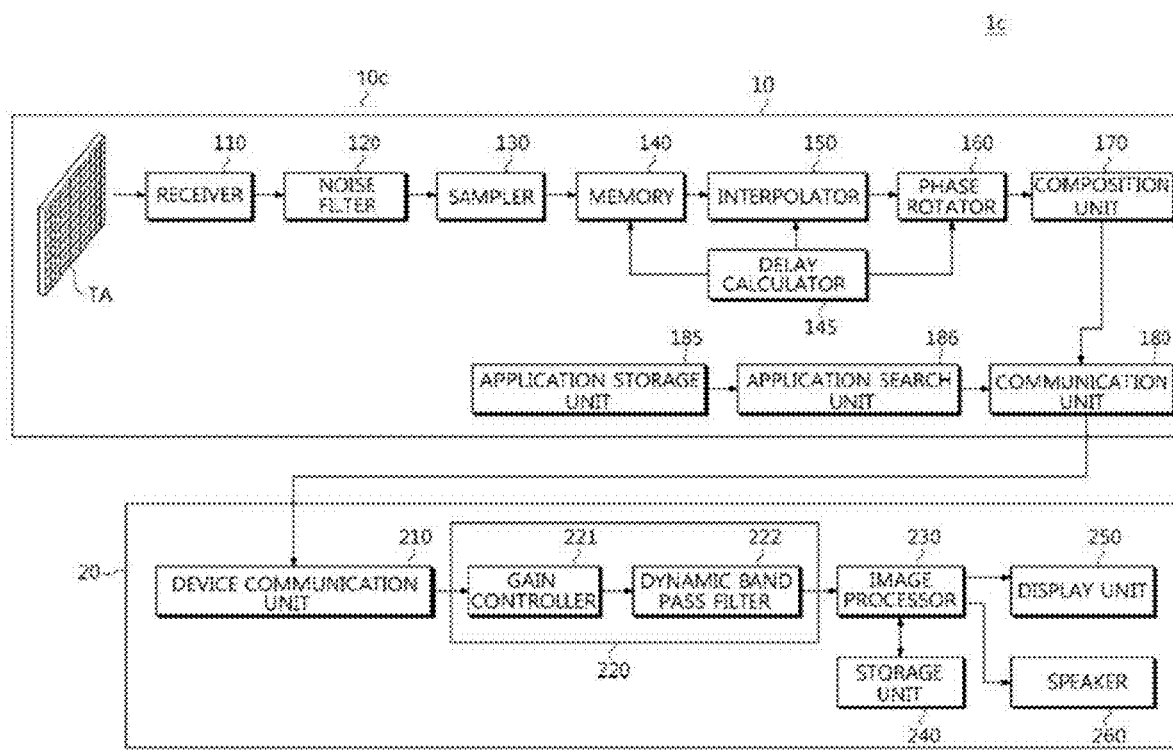
FIG. 9 is a control block diagram illustrating an ultrasound diagnosis system in accordance with another exemplary embodiment.

FIG. 9 is a control block diagram illustrating an ultrasound diagnosis system in accordance with another exemplary embodiment. Among components described in connection with FIG. 9, the same components as the components of the ultrasound diagnosis system 1 according to an exemplary embodiment described in FIG. 4 may have the same reference numerals as the ultrasound diagnosis system 1 according to an exemplary embodiment, and a detailed description thereof will be omitted.

Referring to FIG. 9, a portable ultrasound apparatus 10c of an ultrasound diagnosis system 1c according to another exemplary embodiment may further include an application storage unit 185 and an application search unit 186. When the user terminal 20 generates and displays an ultrasound image by using general purpose hardware, the pre-process of a composite signal, the generation of an ultrasound image, and the display of an ultrasound image may be performed by an application operated in the general purpose hardware, and thus the portable ultrasound apparatus 10c may store an application to be operated in the user terminal 20, and transmit the stored application to the user terminal as needed or desired.

Particularly, the application storage unit 185 may store an application needed for the generation of an ultrasound image, and the display of an ultrasound image. The application may be provided according to an operating system of the user terminal 20 and the performance of the hardware. The application storage unit 185 may be implemented as a High-Speed Random Access Memory, a magnetic disk, SRAM, DRAM, ROM, or the like, but is not limited thereto.

The application search unit 186 may search whether an application of the user terminal 20 connected via the communication unit 180 is installed or not. Particularly, when the user terminal 20 is connected via the communication unit 180, the application search unit 186 may determine whether an application is installed in the user terminal 20, and may install the application in the user terminal 20 when the application is not installed.

In addition, the application search unit 186 may determine whether a new version of an application is installed in the user terminal 20, and may update an application to the new version when a new version of an application is not installed.

As mentioned above, a plurality of applications may be provided according to the operating system and the performance of the hardware of the user terminal 20, and the application search unit 186 may search an application to be installed in the user terminal 20 among the plurality of applications stored in the application storage unit 185.

Figure 10:
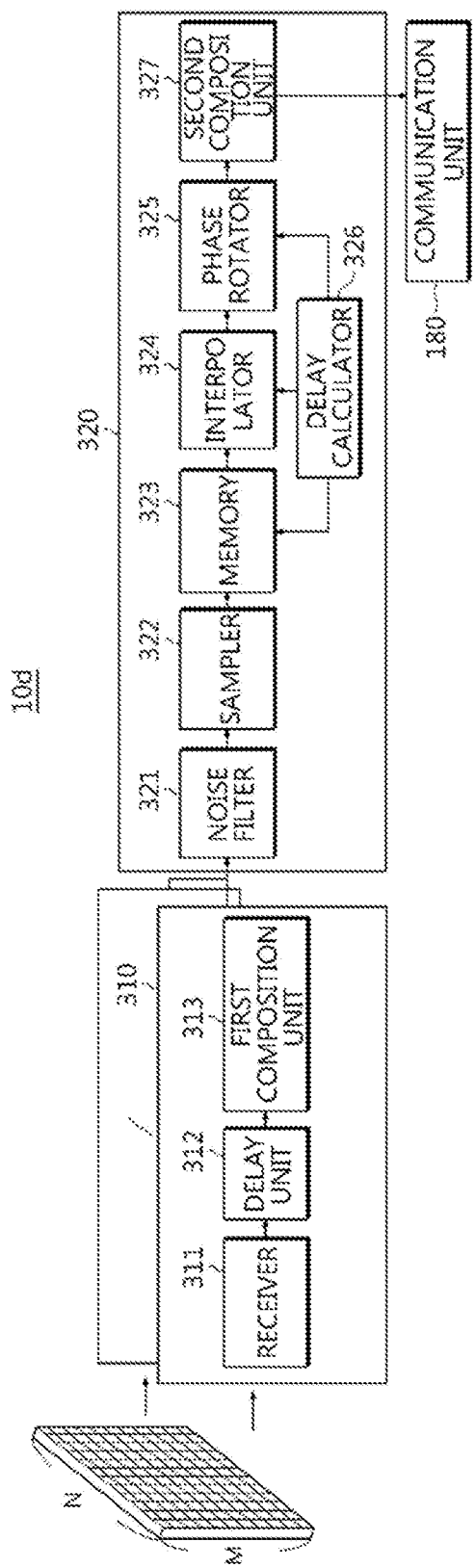
FIG. 10 is a control block diagram illustrating an ultrasound diagnosis system in accordance with another exemplary embodiment.

FIG. 10 is a control block diagram illustrating an ultrasound diagnosis system in accordance with another exemplary embodiment. A portable ultrasound apparatus 10d in FIG. 10 may perform a first beamforming by classifying a plurality of transducer elements into a plurality of sub-groups, and may perform a second beamforming by using a result of the first beamforming.

Referring to FIG. 10, the portable ultrasound apparatus 10d may include a first beamformer 310, a second beamformer 320, and a communication unit 180 (e.g., communicator).

The transducer element of the TA may be classified into a plurality of sub-groups. For example, the TA configured as N×M(M, N≥1) transducer elements arranged in two dimensions may be classified into N sub-groups with respect to each column. When the transducer elements are classified into N sub-groups with respect to a column, each sub-group may include M transducer elements.

The first beamformer 310 may be provided in each sub-group. The first beamformer 310 may be connected to a plurality of transducer elements forming a single sub-group, and generate a first composite signal by beamforming an echo signal outputted from a transducer element forming a sub-group.

Particularly, the first beamformer 310 may include a receiver 311, a delay unit 312 (e.g., delayer), and a first composition unit 313 (e.g., first compositioner) to perform beamforming in an analog manner. At this time, the receiver 311 and the delay unit 312 may be provided in each channel of the transducer element forming a sub-group. For example, when a single sub-group is composed of M transducer elements, the first beamformer 310 may be provided with M receivers 311 and M delay units 312.

The receiver 311 may amplify an echo signal outputted from each channel of each transducer element, and output the amplified echo signal.

Due to a distance difference between the focal point and each transducer element, an echo signal may be inputted to the receiver 311 with a certain time difference. The delay unit 312 may output an echo signal with a time delay as much as a time difference caused by a distance difference between the focal point and each transducer element, and thus may compensate the time difference caused by the distance difference between the focal point and each transducer element. The delay unit 312 may be implemented as a mixer to delay the output of the echo signal, but is not limited thereto.

The first composition unit 313 may output a first composite signal by composing a plurality of echo signals outputted from a plurality of delay units 312. The first composition unit 313 may compose the plurality of echo signals by applying a certain weighted value.

The second beamformer 320 may generate a second composite signal by focusing a plurality of first composite signals outputted from a plurality of first beamformers 310.

Particularly, the second beamformer 320 may include a noise filter 312, a sampler 322, a memory 323, an interpolator 324, a phase rotator 325, a delay calculator 326 and a second composition unit 327 (e.g., second compositioner). The noise filter 321, the sampler 322, the memory 323, the interpolator 324, the phase rotator 325, and the delay calculator 326 may be provided in a number as many as the number of the first beamformer 310.

The second beamformer may generate the second composite signal in the same method as the method of the beamformer of FIG. 4.

Particularly, the sampler 322 may sample an in-phase signal and a quadrature signal from a first composite signal by using a sampling frequency, and store the sampling signal in the memory 323. The sampling signal stored in the memory 323 may be outputted according to a coarse delay, which is calculated by the delay calculator 326.

The sampling signal outputted from the memory 323 may be interpolated by the interpolator 324 to be inputted to the phase rotator 325. The phase rotator 325 may convert a fine delay, which is calculated by the delay calculator 326, into the form of a phase delay, and apply the fine delay to the interpolated sampling signal.

The second composition unit 327 may generate a second composite signal by composing the sampling signal, to which a fine delay is applied by a plurality of phase rotators 325.

As mentioned above, by dividing the beamforming into several steps, the complexity of hardware for the beamforming may be reduced, and the beamforming may be performed fast.

Figure 11:
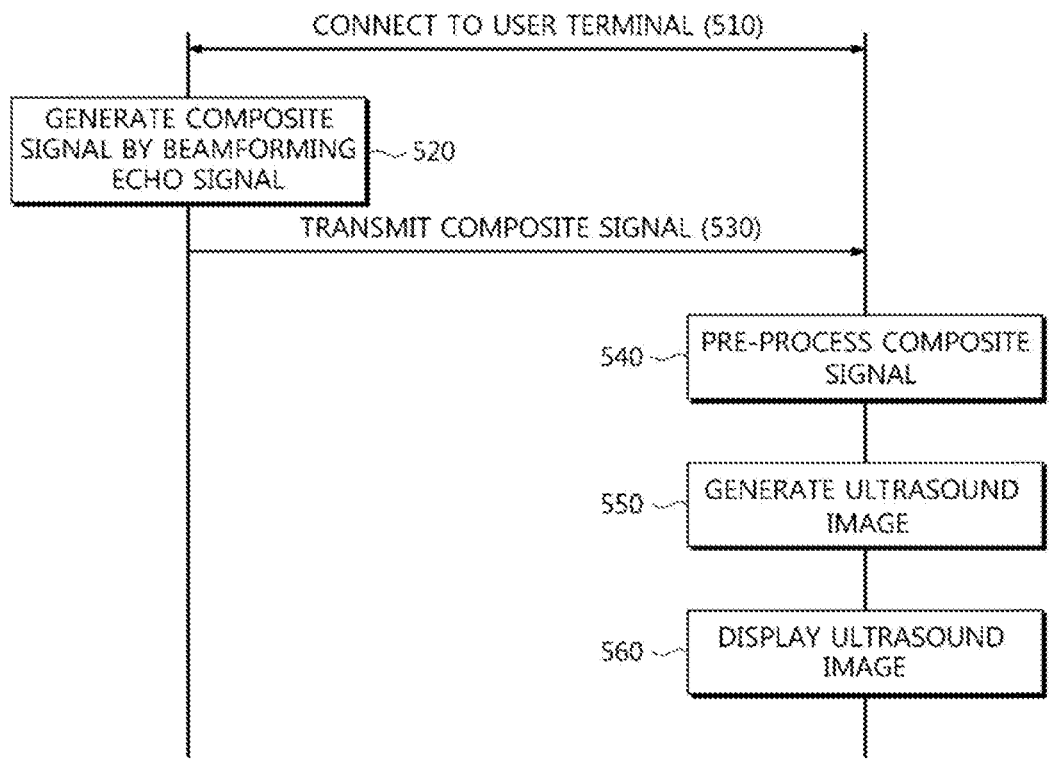
FIG. 11 is a flow chart illustrating a control method of an ultrasound diagnosis system in accordance with another exemplary embodiment.

FIG. 11 is a flow chart illustrating a control method of an ultrasound diagnosis system in accordance with an exemplary embodiment.

Referring to FIG. 11, the portable ultrasound apparatus 10 may be connected to the user terminal 20 in operation 510. The portable ultrasound apparatus 10 and the user terminal 20 may be connected by at least one of a wired communication method, a local communication method, and a wireless communication method, and the user terminal 20 may display a certain screen, which is to be connected to the portable ultrasound apparatus 10.

The portable ultrasound apparatus 10 may generate a composite signal by beamforming an echo signal reflected from an object in operation 520. The portable ultrasound apparatus 10 may sample an in-phase signal and a quadrature signal from the echo signal by using a sampling frequency, and may generate a composite signal by applying a coarse delay and a fine delay to the sampled in-phase signal and quadrature signal. A detailed description of the beamforming method will be described with reference to FIG. 12.

The composite signal generated in the portable ultrasound apparatus 10 may be transmitted to the user terminal 20 in operation 530. The composite signal may be transmitted to the user terminal 20 after being divided into a certain size, and being compressed.

The portable ultrasound apparatus 10 may reduce a sampling frequency prior to the transmission the composite signal. The portable ultrasound apparatus 10 may adjust a sampling cycle of the composite signal to be bigger so that the sampling frequency of the composite signal may be reduced.

The user terminal 20 may perform a pre-process of the received composite signal in operation 540. For example, the user terminal 20 may control a gain of the composite signal, and may compensate the frequency variation, which is variable according to the depth of the focal point, by using the dynamic band pass filter 222 (refer to FIG. 4). The depth of the focal point may be set by a user and a pass band of the dynamic band pass filter 222 may be adjusted according to the depth of the focal point. Accordingly, the center frequency variation generated according to the depth of the focal point may be compensated.

The user terminal 20 may generate an ultrasound image based on a pre-processed composite signal in operation 550. For example, the user terminal 20 may remove a clutter signal from the pre-processed composite signal, and may extract a spectrum component by performing a Fast Fourier Transform on the composite signal in which a clutter signal is removed. The user terminal 20 may generate a D-mode image or a C-mode image by using the extracted spectrum component.

In addition, the user terminal 20 may perform a Hilbert Transform on the composite signal in which a clutter signal is removed, to extract a forward frequency and a reverse frequency of the blood flow.

The user terminal 20 may display an ultrasound image in operation 560. At this time, the forward frequency and the reverse frequency of the blood flow acquired by Hilbert Transform may be converted into a certain sound, and the sound may be provided together with an ultrasound image.

Also, FIG. 11 illustrates that the user terminal 20 pre-processes the composite signal, but the pre-process of the composite signal may be performed by the portable ultrasound apparatus 10b, as illustrated in FIG. 8.

Figure 12:
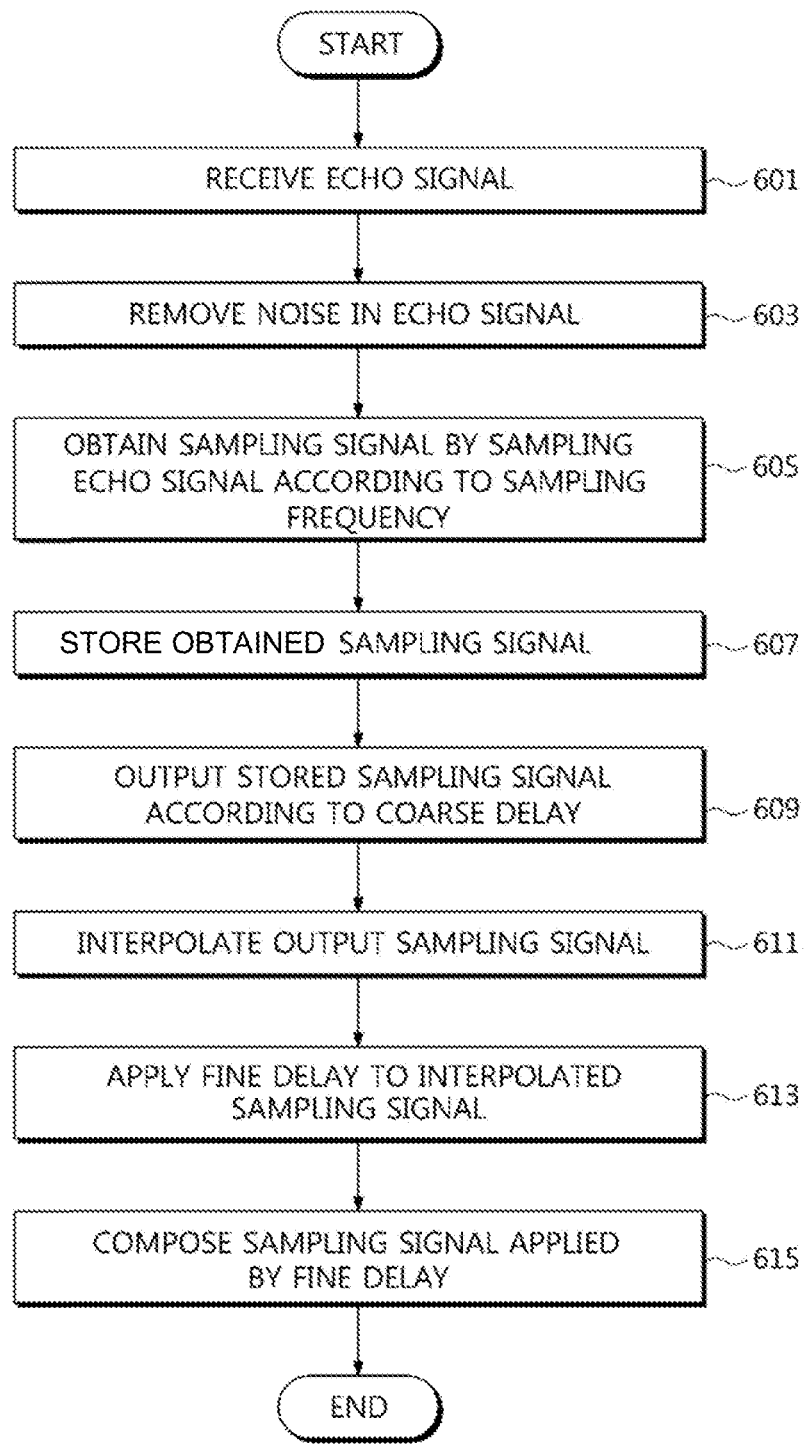
FIG. 12 is a flow chart illustrating an example of beamforming of FIG. 11.

FIG. 12 is a flow chart illustrating an example of the beamforming of FIG. 11.

Referring to FIG. 12, the portable ultrasound apparatus 10 may receive an echo signal reflected from an object in operation 601. The received echo signal may be amplified. For the amplification of the echo signal, any amplifier among a Low Noise Amplifier (LNA), a Variable Gain Amplifier (VGA), and a Time Gain Compensation amplifier (TGC) may be used.

The portable ultrasound apparatus 10 may remove noise from the echo signal in operation 603. The noise may be removed by the low band pass filter.

The portable ultrasound apparatus 10 may extract a sampling signal by sampling an echo signal according to a sampling signal in operation 605. The sampling signal may include an in-phase signal and a quadrature signal, and the sampling frequency may represent the number of samples per time unit. The sampling frequency may be determined by the sampling theory, and may be determined as a sampling frequency which enables an in-phase signal and a quadrature signal to be directly extracted from an echo signal without a demodulation process.

The portable ultrasound apparatus 10 may store the extracted sampling signal 607. The sampling signal may be stored in an interleaved manner. Particularly, when using the sampling frequency, the in-phase signal and the quadrature signal may be extracted in an interleaved manner. As mentioned above, when the in-phase signal and the quadrature signal are extracted in an interleaved manner, the in-phase signal and the quadrature signal may be stored in an interleaved manner.

The portable ultrasound apparatus 10 may output the stored sampling signal according to a coarse delay in operation 609. Due to a distance difference between the focal point and a transducer element, a point in time when an echo signal is outputted from each transducer element may be different from each other. The portable ultrasound apparatus 10 may output a sampling signal by applying a coarse delay and thus may compensate a time difference caused by the distance difference between the focal point and a transducer element.

The portable ultrasound apparatus 10 may perform an interpolation on the outputted sampling signal in operation 611. Particularly, the portable ultrasound apparatus 10 may perform zero padding to input an interpolation signal, that is 0 (zero), between the sampled signals, and may increase a sampling frequency by passing a sampling signal, in which the interpolation signal is inserted, through the interpolation filter.

The portable ultrasound apparatus 10 may apply a fine delay to an interpolated sampling signal in operation 613. The fine delay is configured to compensate a smaller time difference than a sampling cycle. The portable ultrasound apparatus 10 may convert the fine delay into the form of a delay phase, and may apply the fine delay by rotating a phase of the sampling signal as much as the delay phase.

The portable ultrasound apparatus 10 may compose the sampling signal, to which the fine delay is applied, in operation 615. When the sampling signal is composed, a weighed value may be applied.

Also, while FIG. 12 illustrates an example of a beamforming method, a beamforming method of the portable ultrasound apparatus 10 according to other exemplary embodiments is not limited thereto. For example, as illustrated in FIG. 10, after performing a first beamforming on a sub-group, a second beamforming may be performed by performing operations 605 to 615 illustrated in FIG. 12.

Figure 13:
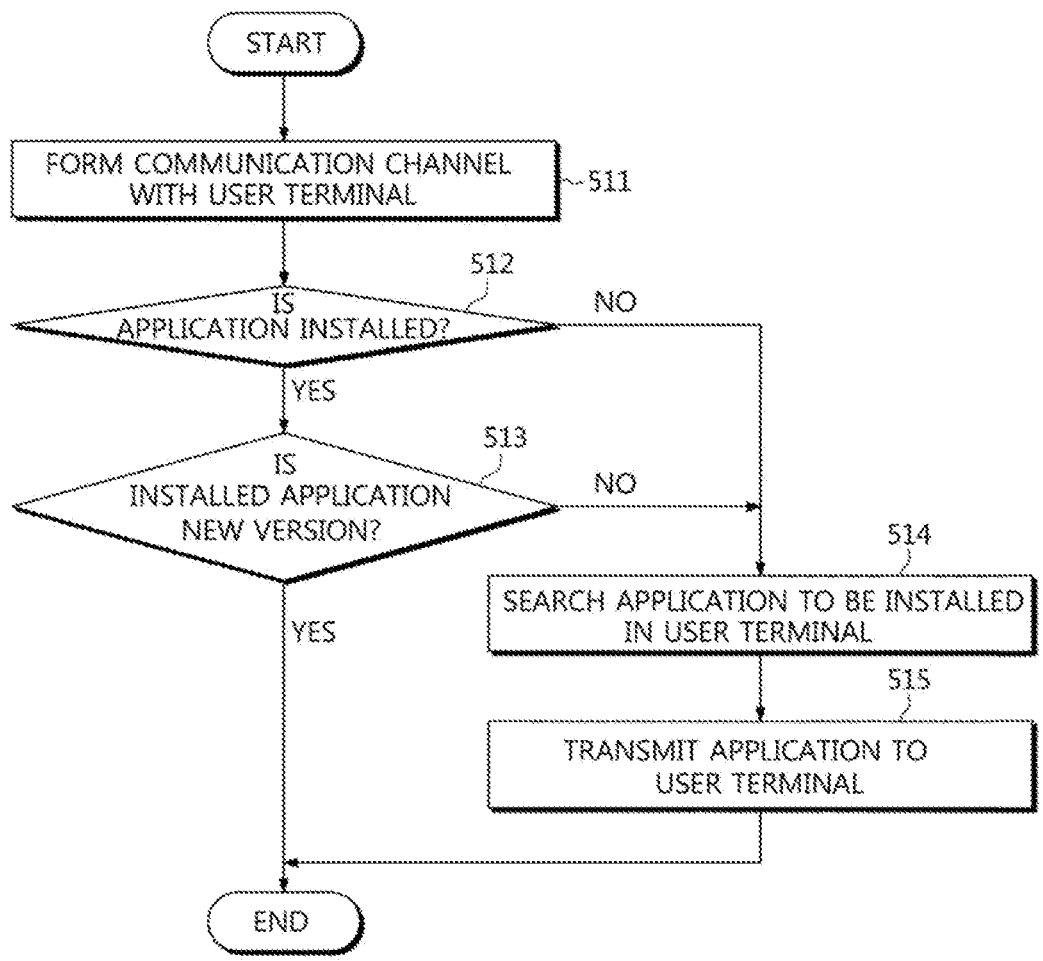
FIG. 13 is a flow chart illustrating operation 510 of FIG. 11 in detail.

FIG. 13 is a flow chart illustrating operation 510 of FIG. 11 in detail.

Referring to FIG. 13, the portable ultrasound apparatus 10 may form a communication channel with the user terminal 20 in operation 511.

When the communication channel is set, the portable ultrasound apparatus 10 may determine whether an application is installed in the user terminal 20 in operation 512. Particularly, the portable ultrasound apparatus 10 may request information related to an application to the user terminal 20, and may determine whether an application is installed in the user terminal 20 by using the information received from the user terminal 20.

When an application is installed in the user terminal 20 (YES of 512), the portable ultrasound apparatus 10 may determine whether the application installed in the user terminal 20 is a new version in operation 513. The portable ultrasound apparatus 10 may determine whether the application is a new version based on version information of the application, application installation date, or the like.

Meanwhile, when an application is not installed in the user terminal 20 (NO of 512), or when an application installed in the user terminal 20 is not a new version (NO of 513), the portable ultrasound apparatus 10 may search an application to be installed in the user terminal 20 in operation 514. Particularly, the portable ultrasound apparatus 10 may search an application to be installed in the user terminal 20 based on hardware and an operating system of the user terminal 20.

The portable ultrasound apparatus 10 may transmit the application to the user terminal 20 in operation 515. The user terminal 20 may install the received application.

As is apparent from the above description, according to the proposed portable ultrasound apparatus and the control method thereof according to exemplary embodiments, an efficiency in beamforming of a sampled signal may be improved.

Although a few exemplary embodiments have been shown and described, it would be appreciated by those skilled in the art that changes may be made in these exemplary embodiments without departing from the principles and spirit of the disclosure, the scope of which is defined in the claims and their equivalents.

What is claimed is:

1. A portable ultrasound apparatus comprising:
 a transducer array configured to transmit an ultrasound signal to an object;
 a memory configured to store an application that is configured to be executed by a user terminal to generate an ultrasound image from an in-phase composite signal and a quadrature composite signal; and
 one or more processors configured to:
  transmit the application to the user terminal;
  obtain an in-phase signal and a quadrature signal from an echo signal reflected from the object;
  store the in-phase signal and the quadrature signal and output the stored in-phase signal and the stored quadrature signal according to a first time delay;
  interpolate the in-phase signal and the quadrature signal outputted from the memory;
  apply a second time delay to the interpolated in-phase signal and the interpolated quadrature signal;
  generate the in-phase composite signal and the quadrature composite signal based on the in-phase signal and the quadrature signal, to which the second time delay is applied, respectively; and
  transmit the in-phase composite signal and the quadrature composite signal to the user terminal to permit the user terminal to generate the ultrasound image using the application.

2. The portable ultrasound apparatus of claim 1, wherein:
 the one or more processors are configured to interpolate the in-phase signal and the quadrature signal based on the second time delay.

3. The portable ultrasound apparatus of claim 1, wherein:
 the one or more processors are configured to convert the second time delay into a form of a delay phase, and apply the delay phase to the in-phase signal and the quadrature signal.

4. The portable ultrasound apparatus of claim 1, wherein:
 the one or more processors are configured to calculate the first time delay and the second time delay based on a focal position of the ultrasound signal, and control the output of the stored in-phase signal and the stored quadrature signal according to the first time delay.

5. The portable ultrasound apparatus of claim 1, wherein:
the one or more processors are configured to focus a plurality of echo signals reflected from the object to obtain the in-phase signal and the quadrature signal.

6. The portable ultrasound apparatus of claim 1, wherein:
the one or more processors are configured to identify whether the application is installed in the user terminal, and determine whether the application is to be installed in the user terminal according to the identification.

7. The portable ultrasound apparatus of claim 1, wherein:
the one or more processors are configured to reduce a sampling frequency in at least one composite signal among the in-phase composite signal and the quadrature composite signal.

8. The portable ultrasound apparatus of claim 1, wherein:
the one or more processors are configured to compensate a frequency variation which changes according to a focal position of the ultrasound signal.

9. The portable ultrasound apparatus of claim 1, wherein:
the one or more processors are configured to receive an input of a focal position of the ultrasound signal.

10. A control method to be performed by a portable ultrasound apparatus, the control method comprising:
transmitting, by the portable ultrasound apparatus and to a user terminal, an application that is configured to be executed by the user terminal to generate an ultrasound image from an in-phase composite signal and a quadrature composite signal;
transmitting, by the portable ultrasound apparatus and via a transducer array, an ultrasound signal to an object;
obtaining, by the portable ultrasound apparatus, an in-phase signal and a quadrature signal from an echo signal reflected by the object, and storing the obtained in-phase signal and the obtained quadrature signal;
performing, by the portable ultrasound apparatus, a first delay operation to output the stored in-phase signal and the stored quadrature signal according to a first time delay;
interpolating, by the portable ultrasound apparatus, the output in-phase signal and the output quadrature signal;
performing, by the portable ultrasound apparatus, a second delay operation to apply a second time delay to the interpolated in-phase signal and the interpolated quadrature signal;
generating, by the portable ultrasound apparatus, the in-phase composite signal and the quadrature, composite signal based on the in-phase signal and the quadrature signal, to which the second time delay is applied, respectively; and
transmitting, by the portable ultrasound apparatus and to the user terminal, the in-phase composite signal and the quadrature composite signal to the user terminal to permit the user terminal to generate the ultrasound image using the application.

11. The control method of claim 10 wherein:
the interpolating comprises:
performing a zero padding operation to insert zero in the in-phase signal and the quadrature signal based on the second time delay, and
filtering the in-phase signal and the quadrature signal, in which the zero is inserted.

12. The control method of claim 10, wherein:
the performing of the second delay operation comprises converting the second time delay into a form of a delay phase, and applying the delay phase to the in-phase signal and the quadrature signal.

13. The control method of claim 10, further comprising:
calculating the first time delay and the second time delay according to a focal position of the ultrasound signal.

14. The control method of claim 10, further comprising:
focusing a plurality of echo signals reflected from the object to obtain the in-phase signal and the quadrature signal.

15. The control method of claim 10, further comprising:
reducing a sampling signal in at least one of the in-phase composite signal and the quadrature composite signal.

16. The control method of claim 10, further comprising:
compensating a frequency variation which changes according to a focal position of the ultrasound signal.

17. The control method of claim 10, wherein:
the storing comprises storing the in-phase signal and the quadrature signal in an interleaved manner.

18. An ultrasound apparatus, comprising:
a transducer array configured to transmit an ultrasound signal to an object;
a memory configured to store an application that is configured to executed by a user terminal to generate an ultrasound image; and
one or more processors configured to:
transmit the application to the user terminal;
sample a signal obtained from an echo signal reflected from the object according to a sampling frequency;
store the sampled signal;
interpolate data in the stored signal, to thereby increase the sampling frequency; and
transmit, to the user terminal the interpolated signal to permit the user terminal to generate the ultrasound image using the application.

19. The ultrasound apparatus of claim 18, wherein the interpolated data comprises zero components.

* * * * *